United States Patent [19]

Tamura et al.

[11] Patent Number: 4,837,313

[45] Date of Patent: Jun. 6, 1989

[54] POLYGALACTOSAMINE PF-192 AND SALTS THEREOF

[75] Inventors: Jun-ichi Tamura; Hiroaki Takagi, both of Chiba, Japan

[73] Assignee: Higeta Shoyu Co., Ltd., Tokyo, Japan

[21] Appl. No.: 10,305

[22] Filed: Feb. 2, 1987

[30] Foreign Application Priority Data

Jun. 12, 1986 [JP] Japan .................................. 61-134799

[51] Int. Cl.$^4$ .......................... C07H 5/04; C07H 5/06; C12R 1/79; C08B 37/00
[52] U.S. Cl. .................................. 536/55.1; 536/18.7; 536/55; 435/932
[58] Field of Search .............. 435/932; 536/18.7, 55.1, 536/55, 55.2, 123

[56] References Cited

U.S. PATENT DOCUMENTS 3,923,782 12/1975 Finn et al. ........................... 435/822
4,683,298 7/1987 Yalpani .............................. 536/18.7

FOREIGN PATENT DOCUMENTS 56-12639 10/1978 Japan .

OTHER PUBLICATIONS

Takagi et al; Agric. Biol. Chem. 49(11): 3151-3157 (1985).
Takagi et al; Agric. Biol. Chem. 49(11): 3159-3164 (1985).

*Primary Examiner*—Ronald W. Griffin
*Assistant Examiner*—Nancy S. Carson
*Attorney, Agent, or Firm*—Browdy and Neimark

[57] ABSTRACT

A natural polymer material PF-102 and salts thereof are widely available as a convenient flocculant for fine suspended matters. PF-102 can be produced by, for example, an imperfect fungus *Paecilomyces* I-1 (FERM BP-1180).

2 Claims, 7 Drawing Sheets

POLYGALACTOSAMINE PF-192 AND SALTS THEREOF

FIELD OF THE INVENTION

This invention relates to a flocculant PF-102, which is highly useful in flocculating fine suspended matters, and salts thereof.

BACKGROUND OF THE INVENTION

Various flocculants including inorganic materials such as ferric chloride and synthetic polymers such as polyacrylamide flocculants have been employed depending on the purpose of the use. However every known flocculant has some disadvantages. For example, an acrylamide monomer from which the polyacrylamide flocculants are produced has an intense toxicity, which causes some troubles from a viewpoint of safety. Namely the process for the production of these flocculants might be dangerous. Further these flocculants might be contaminated with said monomer. The use of ferric chloride as a flocculant in activated sludge might restrict the application of the obtained sludge as a fertilizer. Furthermore the combustion of the sludge thus treated might be harmful and the disposal of the same might be accompanied by residual toxicity. Polysodium acrylate, which is an anionic flocculant, can be applied only in a limited range and is unavailable in flocculating, for example, microorganisms.

Conventional natural polymer flocculants such as chitosan, guar gum, sodium alginate and CMC are disadvantageous because of the limited flocculating capabilities, though they are free from problems such as toxicity and environmental pollution accompanying their disposal.

On the other hand, an increasing demand for flocculants has made it urgently necessary to develop a flocculant which is available for various matters to be flocculated under various conditions including temperature, pH value and the presence of inhibitory materials and which is accompanied by neither toxicity nor disposal problem.

In order to obtain a flocculant satisfying the above requirements, we previously examined various microorganisms. Consequently we found that an imperfect fungus I-1 isolated from humus soil in Wakayama, Japan, accumulated a flocculant, which proved to be completely novel substance and was named PF-101, in a culture filtrate, thus completing the previous invention (cf. Japanese Patent Publication No. 12639/1981).

SUMMARY OF THE INVENTION

However the flocculant PF-101, which will be called PF-101 hereinafter, has various disadvantages in that it can be purified only by a highly complicated process comprising adding ethanol to a culture medium, dissolving the fraction thus precipitated in hot water and adsorbing the same by Sepharose 6B followed by eluting with a malate buffer solution; that this process gives an extremely low recovery; and that the obtained product is hardly soluble in various solvents and inconvenient to treat.

As a result in our studies on the purification of the flocculant from the culture medium, we have found that it can be precipitated by adding salt(s) to the medium, thus completing the present invention.

According to this process, the flocculant can be more conveniently and effectively obtained. We have further found that the flocculant precipitated by adding salt(s) is soluble in an aqueous solution of an acid at room temperature. The precipitate soluble in an aqueous solution of an acid is repeatedly purified to give a substantially pure product. Examination on the physicochemical properties of the pure product suggests that it is a novel substance significantly different from PF-101. Thus we have named this substance PF-102.

BRIEF DESCRIPTION OF THE DRAWINGS

FIG. 1 is an ultraviolet absorption spectrum of hydrochloride of PF-102, while

DETAILED DESCRIPTION OF THE INVENTION

This invention relates to PF-102 and salts thereof.

PF-102 of the present invention is soluble in an aqueous solution of almost every acid to form an acid salt. Although PF-102 can be isolated, it is hardly soluble in an aqueous solution and extremely difficult to handle. Thus the flocculation activity, the pH range of the flocculation activity, the temperature range of the same, the ultraviolet absorption spectrum and color reactions among the physicochemical properties are determined with the use of hydrochloride of PF-102.

PF-102 of the present invention has the following physicochemical properties: (1) Flocculation activity It can flocculate fine suspended matters only with a very small amount thereof. (2) pH range of flocculation activity It shows a stable flocculation activity within the range of pH 2 to 9.

(3) Temperature range of flocculation activity

It shows a flocculation activity within the range of 0° to 100° C.

(4) Ionic strength of flocculation activity

Its flocculation activity is inhibited by carbonic acid and $Fe_2(SO_4)_3$, but never affected by other various ions of various ionic strength, and neither NaCl nor $K_2SO_4$ gives any effect up to a concentration of 1 M.

(5) Elemental analysis

N: 8.64%,

C: 42.80%, and

H: 6.87%.

General formula: $(C_6H_{11}NO_4.xH_2O)_n$.

Figure 1:
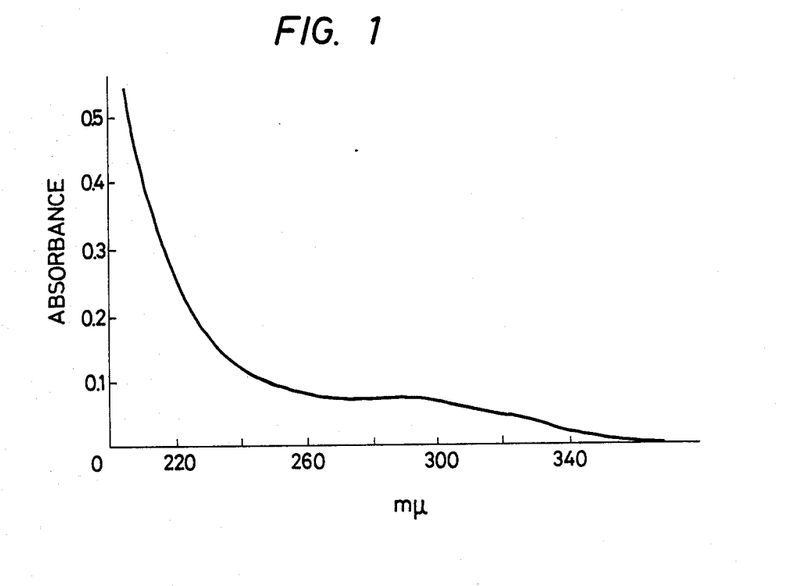

(6) Ultraviolet absorption spectrum as shown in FIG. 1.

Figure 2:
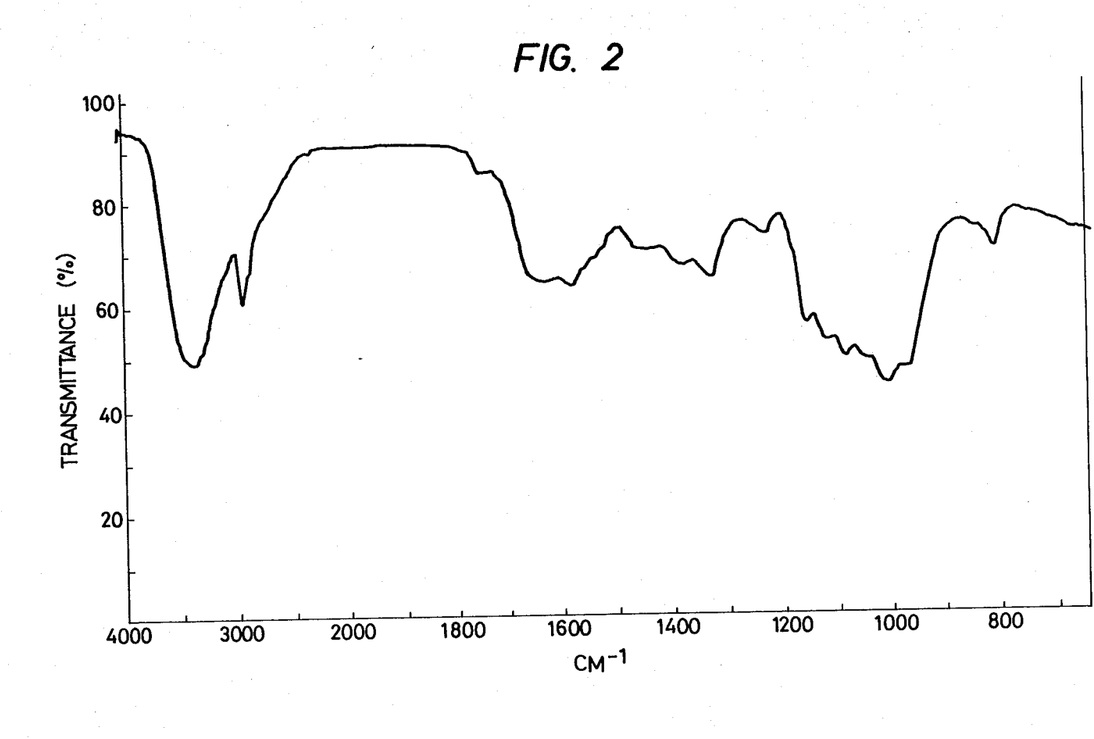
FIG. 2 is an infrared absorption spectrum of PF-102.
Figure 3:
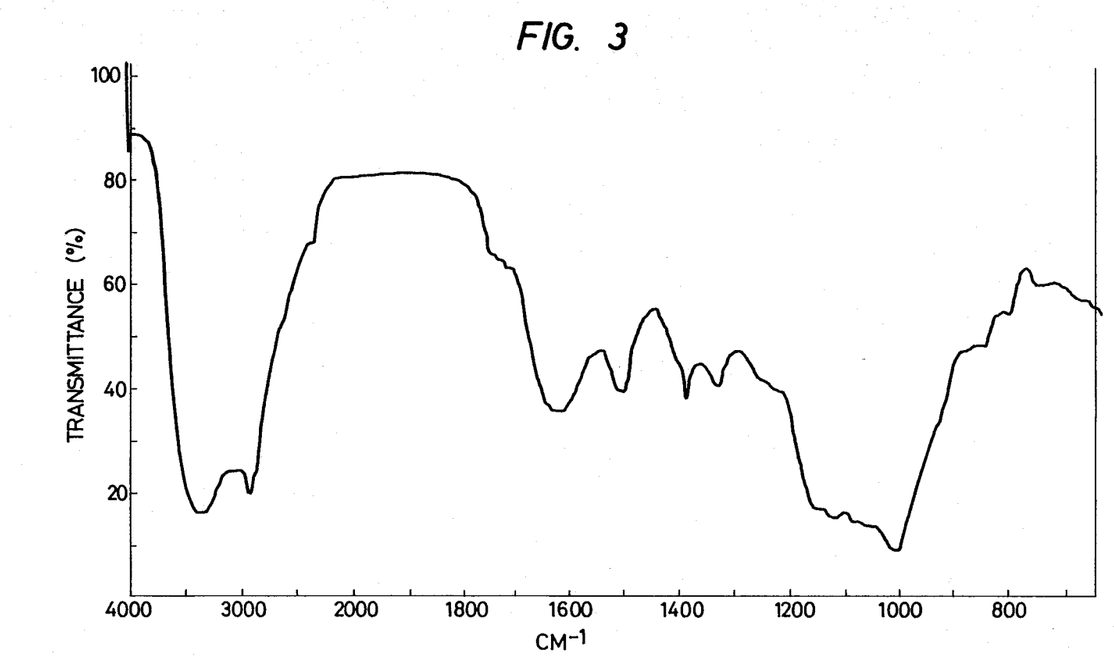
FIGS. 3, 4, 5, 6 and 7 are infrared absorption spectra of phosphate, hydrochloride, acetate, lactate and citrate of PF-102.
Figure 4:
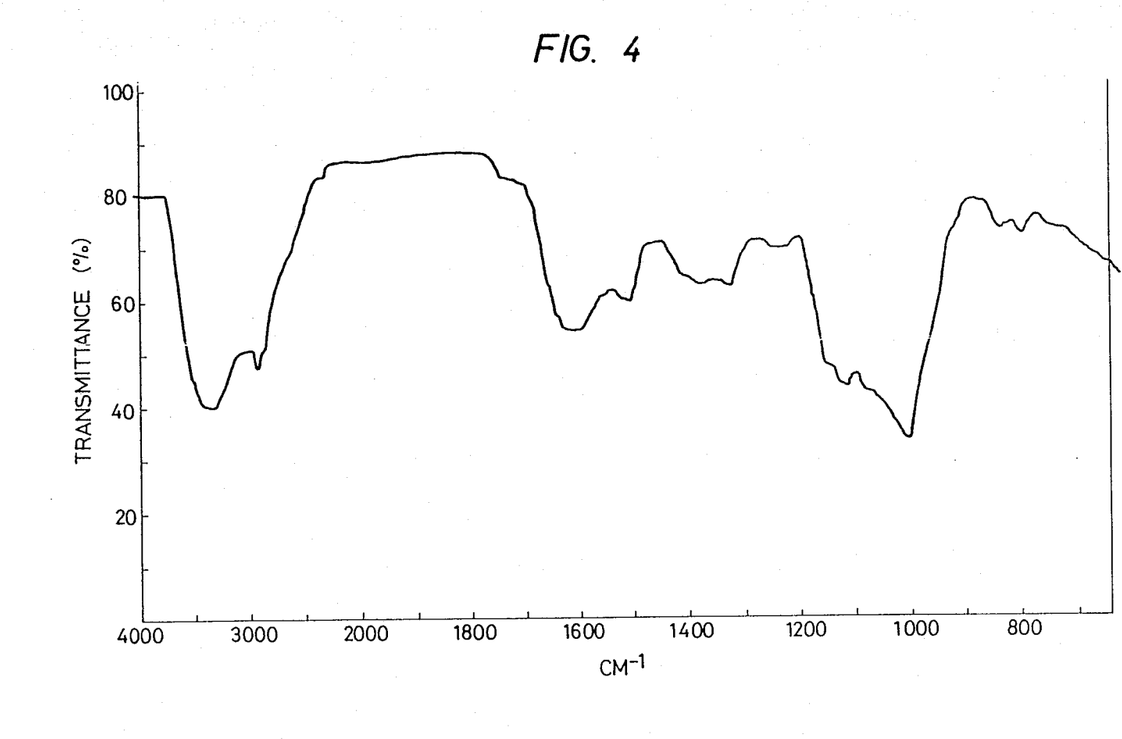
Figure 5:
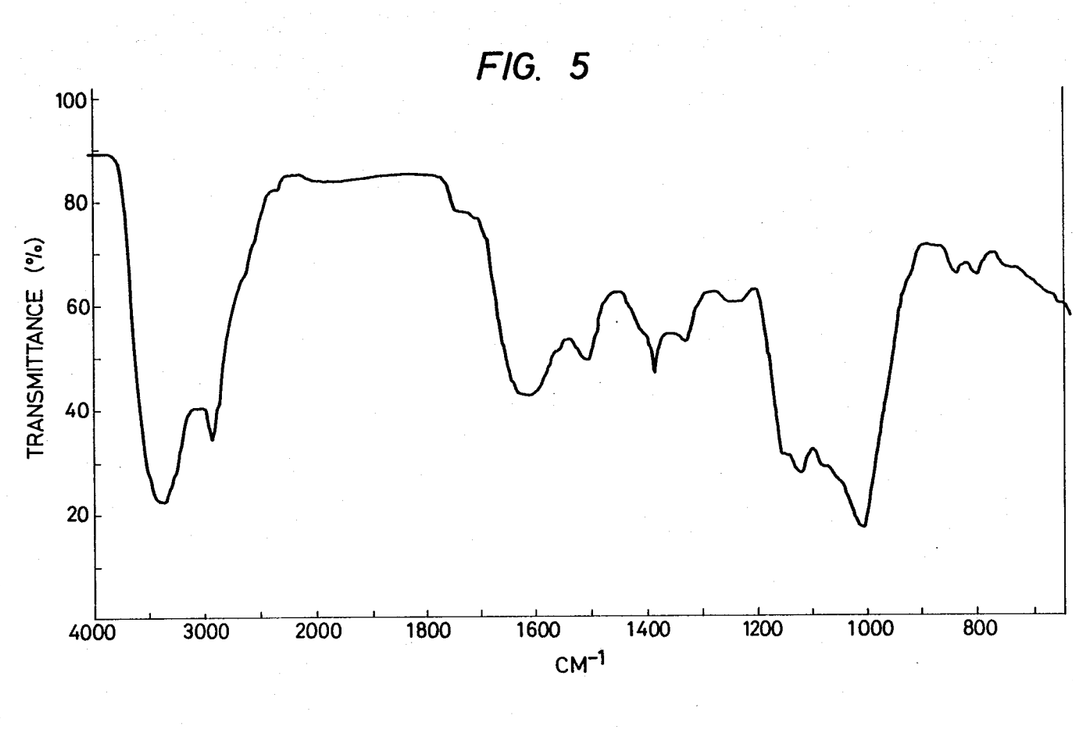
Figure 6:
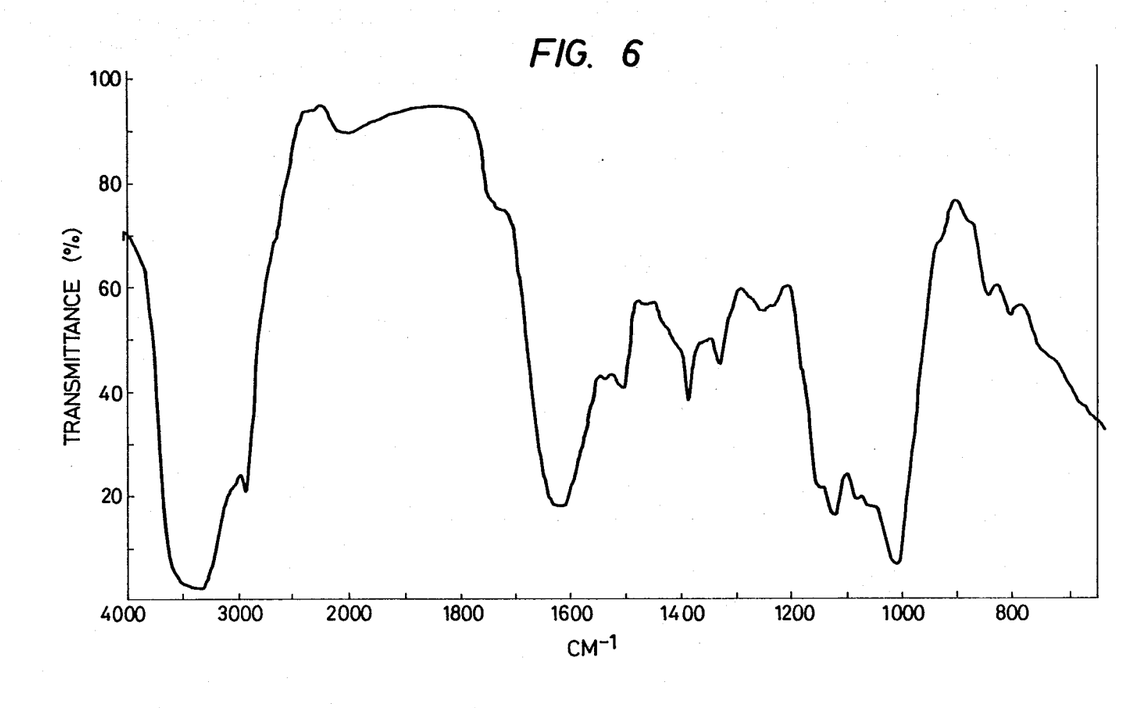
Figure 7:
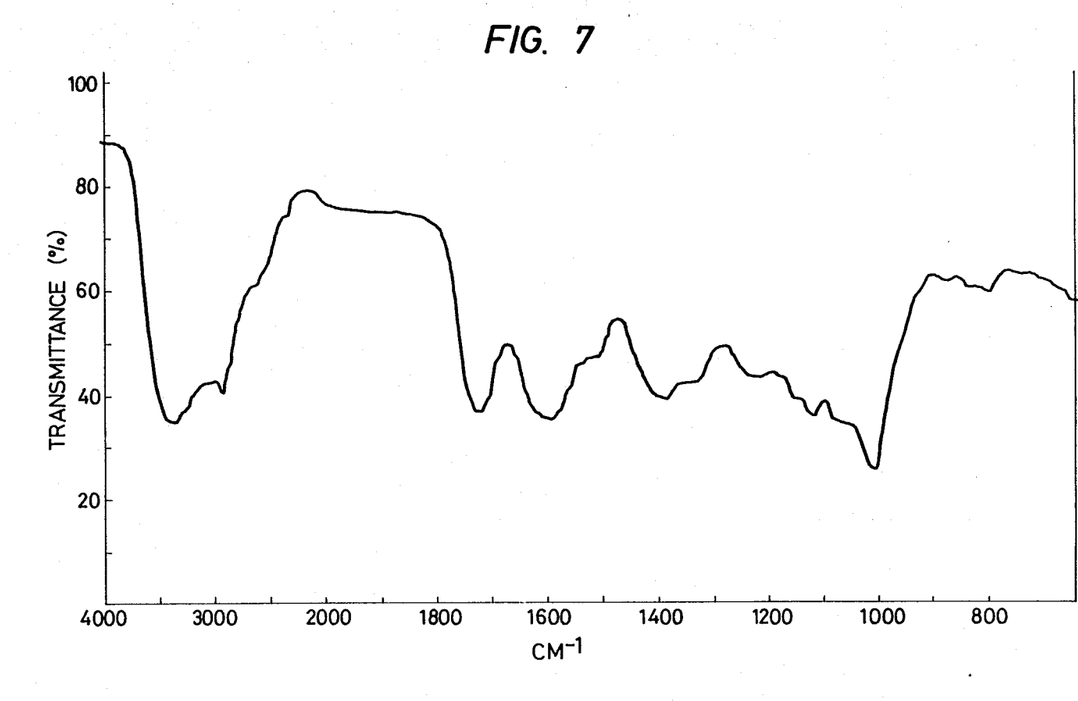

(7) Infrared absorption spectrum as shown in FIG. 2.

(8) Color reactions ninhydrin reaction: +, xanthoprotein reaction: −, Ehrlich reaction: −, Molisch reaction: −, phenol sulfate reaction: ±, and Le Rosen test: −.

(9) Constituents

From hydrolyzed PF-102, only galactosamine was detected as saccharide, no neutral saccharides were detected, and no amino acids were detected. This teaches that PF-102 is a polymer comprising galactosamine. The main linkage is considered to be an α1–4 linkage from the results of the measurement of specific rotatory power, periodate oxidation, and Smith's decomposition treatment.

(10) Electrophoresis

It is confirmed as a single substance by density-gradient isoelectric focusing showing an isoelectric point (pI) of 8.5.

(11) Color of the substance, Pale yellow.
(12) Basicity, acidity or neutrality

It shows a pH value of 7.5 when suspended in water at a concentration of 0.5 % w/v (pH value of deionized water being 5.8).

(13) Solubility in solvents:
Hardly soluble in hot water.
Hardly soluble in cold water.
Highly soluble in a diluted acid.
Hardly soluble in a diluted alkali.
Insoluble in alcoholes, acetone, chloroform, benzene and $\eta$-pentane.

(14) Average molecular weight at least 160,000.

Preferable examples of the acid salt of PF-102 of the present invention are phosphate, hydrochloride, acetate, lactate and citrate. FIGS. 3, 4, 5, 6 and 7 show the infrared absorption spectra of phosphate, hydrochloride, acetate, lactate and citrate of PF-102, respectively.

An acid salt of PF-102 according to the present invention shows a high flocculation activity which makes it useful as a flocculant. Further PF-102, which is a highly purified polysaccharide, is largely expected to be available as an active substance in vivo in the field of pharmaceuticals and agricultural chemicals.

The flocculant PF-102 of the present invention can be produced, for example, by the imperfect fungus I-1 isolated from humus soil in Wakayama by us. The imperfect fungus I-1 belonging to the genus *Paecilamyces* has been named *Paecilomyces* I-1 and deposited with the Fermentation Research Institute (FERM BP-1180, FERM-P No. 3928).

*Paecilamyces* I-1 has the following mycological properties:

(a) Microscopic observation

It has no conidiphore and shows conidia forming a long chain at the end of each phialide which individually comes out directly from a vegatative hypha or hyphae. The phialide, which is semitransparent and 20 to 45$\mu$ in length, has a somewhat wide base (1.0 to 1.5$\mu$) and a somewhat narrow end (0.5 to 1.0$\mu$). It has a linear form or, sometimes, a slightly curved end. Microscopic examination of a conidium indicates that it has a cigar-like or rod-like form and 4–6×1.0–1.4$\mu$ in size.

A chain usually comprises 25 to 35 conidia or, in some cases, more. This chain is very fragile and liable to be broken even with a slight impact.

(b) Growth in various media (plate culture at 25° C.)

(1) Czapek agar medium

A colony shows excellent growth and acquires a size of approximately 45 mm in diameter of the 14th day. A colony has an appearance like white velvet or wool with a gregariously swollen center and a circular edge. Neither waterdrop nor wrinkle is observed. The reverse side of the colony is white at the early stage of the incubation and then turns yellow at the center at the later stage thereof. No pigment is produced in the agar.

(2) Malt agar medium

A colony shows excellent growth and acquires a size of approximately 54 mm in diameter on the 14th day. The edge of the colony is not circular but corrugated. The center of a colony is white and the neighborhood is pale yellow. The colony has a medium thickness with a somewhat sunken center. Neither waterdrop nor wrinkle is observed. The reverse side of the colony is pale yellow as a whole. A pale yellow pigment is produced in the agar medium.

(3) Potato dextrose agar medium

A colony shows remarkably excellent growth and acquires a size of approximately 60 mm in diameter on the 14th day. A signficantly thick colony having an appearance like white velvet or wool is formed. The center is somewhat swollen and surrounded by a slightly thinner pale yellow colony and further by a relatively thick white colony. No wrinkle but several pale brown waterdrops are observed on the surface. The reverse side of the colony shows several radiated wrinkles and concentric deep and pale yellow colors. Diffusion of a pale yellow pigment to the agar is observed.

(4) YpSs agar medium (composition: 1.5% of starch; 0.4% of yeast extract, 0.1% K$_2$HPO$_4$, 0.05% of MgSO$_4$ and 2% of agar)

A colony shows an excellent growth and acquires a size of approximately 50 mm in diameter on the 14th day. A colony is thick and puffy like wool as a whole. Neither waterdrop nor wrinkle is observed. The reverse side of the colony shows no particular characteristic. No pigment is produced.

(5) MY$_{20}$ agar medium (composition: 20% of glucose, 0.5% of peptone, 0.3% of east extract, 0.3% of malt extract and 2% of agar)

A colony shows somewhat poor growth and acquires a size of approximately 30 mm on the 14 day. Few hyphae and a number of fine wrinkles are observed. The center is pale brown and surrounded by a pale yellow portion. The reverse side of the colony is pale yellow with fine wrinkles. No pigment is produced.

These morphological and cultural characteristics suggest that it is an imperfect fungus of monophialide. Many of these characteristics are similar to those of *Paecilomyces bacillisporus* reported by Agnes H. S. Onionsand and G. L. Barron (cf. Monophialidic Species of *Paecilomyces*, Mycological Papers No. 107, Common Wealth Mycological Institute, Kew, England (1967)).

That is to say, this strain has conidia, which is believed to be the most important in the classification of imperfect fungi (*Deuteromycetes*), extremely similar from a morphological viewpoint to those of *P. bacillisporus*. Further the morphology of the phialide of the former is closely similar to that of the latter. However the former shows somewhat different cultural characteristics in various media from the latter. Namely, it is described in the paper as cited above that *P. bacillisporous* grows relatively slowly and that the hyphae of this strain are white at the early stage and become pinkish at the later stage of the incubation. In contrast thereto, the hyphae of the tested strain are white at the early stage and become pale yellow at the later stage of the incubation in some media. However the above paper describes that strains of *P. bacillisporous* show variation in cultural characteristics and in spore size. Thus it is assumed that the tested strain may be *P. bacillisporus* or the one relating thereto. However it has been referred to as *Paecilomyces* I-1 since there is no decisive factor.

The physiological properties of this strain are as follows, though they are regarded as less important in the classification of imperfect fungi.

(c) Physiological properties

(1) Utilization of carbon source

Czapek medium is used as a base medium and the sucrose contained therein is replaced by various carbon sources. As a result, it is found that this strain highly utilizes soluble starch, glycogen, trehalose, raffinose, cellobiose, maltose, sucrose, glucose, fructose, galactose, mannose, inositol, sorbitol and glycerol.

It significantly utilizes inulin, lactose, arabinose, ribose, mannitol, lactic acid and succinic acid, slightly utilizes xylose, rhamnose and citric acid and never utilizes tartaric acid and oxalic acid.

(2) Utilization of nitrogen source

Czapek medium is used as a base medium and the nitrogen source thereof is replaced by various nitrogen sources. As a result, it is found that this strain highly utilizes nitrogen in the forms of ammonia and amino compounds and nitric acid.

(3) Growth temperature

The optimum growth temperature of this strain is 23° to 25° C. It grows at 30° C. but can not grow at 35° C.

(4) Growth pH

This strain is incubated in G. Ye medium comprising 2% of glucose and 0.2% of yeast extract within the range of pH value of 2 to 10. As a result, it shows excellent growth at every pH value.

The strain producing the flocculant PF-101 may be incubated in a liquid medium in a conventional manner employed for the incubation of molds.

Spores or hyphae of the strain producing the flocculant PF-101 are inoculated to a liquid medium and incubated under an aerobic condition. Glucose, maltose, sucrose, starch and blockstrap molasses are available as the carbon source. Among these materials, glucose is preferable. Inorganic nitrogen compounds such as ammonium sulfate and sodium nitrate and organic nitrogen materials such as peptone and yeast extract are available as the nitrogen source.

The incubation temperature may be varied within the range where the flocculant-producing strain can produce the flocculant. It is usually preferable to incubate it at 20° to 25° C. The incubation period varies depending on the incubation condition. The incubation may be generally continued for four to five days and appropriately completed when the accumulation of the flocculant reaches the maximum. Then the culture filtrate is concentrated in vacuo or by ultrafiltration and an organic solvent such as ethanol is added to the obtained concentrate. Thus PF-101 described in Japanese Patent Publication No. 12639/1981 is obtained as a precipitate.

In the present invention, various salts are added to the culture filtrate or the concentrate of the same. When no precipitate is formed thereby, an alkali is added to give a pH value of 7 to 9, thus forming a precipitate. The obtained precipitate is isolated, washed with water and dissolved in a diluted aqueous solution of an acid. Then a preipitate is formed again by adding salt(s) again or adding an alkali to give a pH value of 7 to 9. Thus PF-102 can be obtained in a highly purified form.

One or more salts selected from among the following salts may be added to the solution containing PF-102.

The examples of the salt are hydrochlorides such as potassium chloride, sodium chloride, calcium chloride and ammonium chloride; nitrates such as potassium nitrate and sodium nitrate; acetates such as sodium acetate; sulfates such as dipotassium sulfate, ammonium sulfate, calcium sulfate and copper sulfate; and phosphates such as dipotassium phosphate, monopotassium phosphate, disodium phosphate and monosodium phosphate.

The salt to be added may be in any amount so long as it is in solution. It is preferably added in an amount of 0.5 to 50%, still preferably 2 to 40%, based on the solution containing PF-102.

The addition of some salts makes the pH value of the mixture exceeding 7. In such a case, PF-102 precipitated without adjusting the pH value can be isolated.

When no precipitate is formed by adding salt(s), the pH value of the mixture may be adjusted to 7 to 9, preferably around 8.5 corresponding to the isoelectric point of the aimed product.

PF-102 cannot be gotten as precipitate from the culture filtrate or culture concentrate by adjusting the pH value to 7 to 9. However, PF-102 can be precipitated by adding salts, or by adding salts and adjusting the pH value to 7 to 9. In this way, PF-102 is isolated from impurities such as neutral polysaccharides which are produced in the culture at the same time. This precipitate may be isolated by centrifugation or filtration through a filter cloth.

It is surprising that the complete precipitation of PF-102 can be achieved by simply adding salt(s), since no precipitation thereof is observed even by treating a medium at the isoelectric point (pH 8.5).

Since the precipitate contains a large amount of the salt(s), it is desalted by washing with water or a solvent and dissolved in an acid.

Examples of the acid are organic acids such as acetic acid and inorganic acids such as hydrochloric acid. The acid may be used at a concentration of approximately 0.01 to 3 M.

After dissolving the precipitate in the acid, the pH value of the obtained solution is adjusted to 7 to 9, preferably to pH 8.5 corresponding to the isoelectric point of the aimed product, by adding an alkali such as sodium hydroxide thereto to give a precipitate.

In order to further purify, the precipitate may be washed with, for example, water and adjusted to a pH value of 7 to 9 to thereby give a precipitate.

This purification may be repeated. After the completion of the purification, the precipitate is in a substantially pure state. Thus PF-102 is obtained.

Now Test Example and Example of the present invention will be given.

TEST EXAMPLE

*Paecilomyces* I-1 (FERM BP-1180, FERM P-3928) was incubated in a medium comprising 3% of glucose, 0.3% of peptone and 0.5% of $CaCl_2$ (pH 7.0) to give 20 l of a culture filtrate. Then the filtrate was passed through an UF membrane of a fractionation molecular weight of 160,000 under heating to 55° to 60° C. to thereby concentrate the same and remove low molecular weight materials. Thus 10 l of a solution was obtained.

100-ml portions of this clear concentrated culture filtrate were pipetted into 21 tubes and the salts as shown in Table 1 were added thereto. After adjusting the pH value of each mixture as shown in Table 1, the formed precipitate was determined. Table 1 shows the result, wherein the recovery was determined according to the following equation:

$$\text{Recovery} = \frac{\text{weight of precipitate (dry basis)}}{\text{total weight of galactosamine in medium determined by indole/hydrochloric acid method}} \times 100$$

TABLE 1

| Added salt | pH value (adjusted) | Amount (%) | Recovery of PF-102 (%) |
|---|---|---|---|
| 1 none | 8.5 | 0 | 0 |
| 2 K$_2$HPO$_4$ | 8.5 | 5 | 98 |
| 3 KH$_2$PO$_4$ | 8.5 | 5 | 98 |
| 4 Na$_2$SO$_4$ | 8.5 | 5 | 98 |
| 5 MgSO$_4$ | 8.5 | 30 | 58 |
| 6 (NH$_4$)$_2$SO$_4$ | 8.5 | 20 | 93 |
| 7 CuSO$_4$ | 8.5 | 5 | 96 |
| 8 K$_2$SO$_4$ | 8.5 | 5 | 97 |
| 9 CaSO$_4$ | 8.5 | 5 | 47 |
| 10 (NH$_2$)$_2$H$_2$SO$_4$ | 8.5 | 5 | 88 |
| 11 NH$_4$Cl | 8.5 | 5 | 88 |
| 12 NaCl | 8.5 | 20 | 98 |
| 13 KCl | 8.5 | 20 | 81 |
| 14 CaCl$_2$ | 8.5 | 20 | 92 |
| 15 LiCl | 8.5 | 30 | 93 |
| 16 KNO$_3$ | 8.5 | 30 | 52 |
| 17 NaNO$_3$ | 8.5 | 30 | 93 |
| 18 Ca(NO$_3$)$_2$ | 8.5 | 30 | 46 |
| 19 CH$_3$COONa | 8.5 | 30 | 99 |
| 20 (CH$_2$COO)$_2$.2Na | 8.5 | 20 | 86 |
| 21 (CH$_2$COONa)$_2$.C(OH)COONa | 8.5 | 20 | 77 |
| 22 HCOONa | 8.5 | 30 | 95 |
| 23 CH$_3$CH(OH)COONa | 8.5 | 30 | 93 |
| 24 CH$_2$CH(OH)(COONa)$_2$ | 8.5 | 20 | 87 |

EXAMPLE 1

600 g of glucose, 60 g of peptone and 125 g of CaCl$_2$.2H$_2$O were dissolved in 17 l of tap water and the pH value of the solution was adjusted to 7.0 with a conc. solution of NaOH. Then the solution was introduced into a jar fermenter of 30 l in volume.

The liquid medium thus prepared was sterilized under an elevated pressure at an elevated temperature (121° C.) by injecting vapor thereto for 20 minutes. After cooling, this medium (20l in final volume) was sterilely inoculated with *Paecilomyces* I-1 (FERM BP-1180, FERM P-3928), which has been incubated under shaking in 150 ml of a medium of the same composition, i.e., comprising 3% of glucose, 0.3% of peptone and 0.5% of CaCl$_2$ (pH 7.0) in an Erlenmeyer flask of 500 ml in volume at 26° C. for four days, at a ratio of approximately 10%. After the inoculation, the strain was incubated at 27° C. under aeration at a rate of 0.5 VVM and rotating at 200 rpm for five days.

After the completion of the incubation, the medium was filtered through a filter cloth to give 17 l of a culture filtrate. The filtrate, while being heated at 50°-60° C., was passed through an ultrafiltration membrane of 160,000 in fractionation molecular weight (UF Membrane of Tubular Module F type: mfd. by Mitsubishi Engineering Co., Ltd.) to thereby remove lower molecular weight fractions. Thus it was concentrated to give a volume of approximately 3 l. It was further centrifuged at approximately 14000 x G to thereby remove residual cells and thermally denatured protein.

After the completion of the centrifugation, 750 g of common salt, i.e., approximately 25% in concentration was added to 3 l of the clear supernatant and the mixture was stirred. After the salt was dissolved, the pH value of the mixture was adjusted to 7.0 to 8.5 by conc. NaOH. After allowing to stand overnight to sufficiently precipitate the desalted product, the precipitate was collected on a Saran cloth made of a copolymer of vinylidene chloride and vinyl chloride. A large amount of a slightly alkaline water (pH 7.0 or higher) was applied to the desalted product to thereby wash away the excessive common salt and contaminants such as neutral sugars present in the medium.

After washing with water, the desalted product was dissolved in a 0.1 M solution of hydrochloric acid approximately three times as much as the product in volume. Then conc. NaOH was added to the solution and the pH value of the mixture was adjusted to 8.5 corresponding to the isoelectric point of polygalactosamine. After allowing to stand overnight to thereby sufficently precipitate the product, the precipitate was collected on a Saran cloth similar to the one described above and washed with a large amount of tap water. The precipitate washed with water was dissolved in 0.1 M hydrochloric acid again, precipitated at the isoelectric point and repeatedly washed with water to thereby purify the same.

The precipitate thus purified was lyophilized to give 7 g of a purified powder of PF-102 containing polygalactosamine as the main component, i.e., having a purity of 99% as polygalactosamine.

Further some portion of the purified product may be dissolved in 0.1 M hydrochloric acid and fractionated with an ultrafiltration membrane of 300,000 in fractionation molecular weight (XM 300 type; mfd. by Amicon Corporation) to thereby separate into a fraction of 160,000 to 300,000 in average molecular weight and that of 300,000 or more therein, depending on the application.

What is claimed is:

1. An essentially pure polygalactosamine having the following physicochemical properties:
   (1) a hydrochloride which can flocculate fine suspended matters when only a very small amount of said hydrochloride is added to said fine suspended matter;
   (2) a hydrochloride having a stable flocculation activity within the range of pH 2 to 9;
   (3) a hydrochloride having a flocculation activity within the range of 0° to 100° C.;
   (4) a hydrochloride having a flocculation activity which is inhibitied by carbonic acid and Fe$_2$(SO$_4$)$_3$, but is unaffected by other ions, neither NaCl nor K$_2$SO$_4$ inhibiting flocculation up to a concentration of 1 M;
   (5) an elemental analysis as follows:
       N: 8.64%
       C: 42.80% and
       H: 6.87%; and
       a general formula: $(C_6H_{11}NO_4.xH_2O)_n$, where x indicates the degree of hydration and n indicates the degree of polymerization;
   (6) a hydrochloride having an ultraviolet absorption spectrum as shown in FIG. 1;
   (7) an infrared absorption spectrum as shown in FIG. 2;
   (8) a hydrochloride which exhibits the following color reactions:
       ninhydrin reaction: +,
       xanthoprotein reaction: −, Ehrlich reaction: —,
Molisch reaction: —,
phenol sulfate reaction: ± and
Le Rosen test: —;
(9) the production of only galactosamine as saccharide upon hydrolysis of said polygalactosamine without the generation of detectable neutral saccharides or amino acids, a measurement of specific rotatory power, periodate oxidation, and Smith's decomposition treatment producing results typical of an alpha 1-4 main linkage;
(10) an isoelectric point (pI) of 8.5 as confirmed by density-gradient isoelectric focusing;
(11) a pale yellow color;
(12) a pH value of 7.5 when suspended in water at a concentration of 0.5% w/v (pH value of deionized water being 5.8);
(13) solubility as follows:
hardly soluble in hot water;
hardly soluble in cold water;
highly soluble in a diluted acid;
hardly soluble in a diluted alkali;
insoluble in alcohols, acetone, chloroform, benzene and n-pentane;
(14) an average molecular weight of 160,000 to 300,000; and salt(s) thereof.

2. A salt of said polgalactosamine set forth in claim 1, said salt being selected from the group consisting of hydrochloride, sulfate, phosphate, nitrate, lactate, citrate, succinate, malate, formate and acetate.

* * * * *

UNITED STATES PATENT AND TRADEMARK OFFICE
CERTIFICATE OF CORRECTION

PATENT NO.  : 4,837,313
DATED       : June 6, 1989
INVENTOR(S) : TAMURA et al.

It is certified that error appears in the above-identified patent and that said Letters Patent is hereby corrected as shown below:

On the face of the patent:

[54]               Delete "PF-192", insert therefor -- PF-102 --

Column 1, line 2    In title, delete "PF-192", insert therefor -- PF-102 --

Signed and Sealed this

Twenty-third Day of July, 1991

*Attest:*

HARRY F. MANBECK, JR.

*Attesting Officer*         *Commissioner of Patents and Trademarks*